(12) United States Patent
Nasser

(10) Patent No.: US 11,253,165 B2
(45) Date of Patent: Feb. 22, 2022

(54) INTRAVASCULAR MRI PROBE ASSEMBLY

(71) Applicant: Mohammad Nasser, Tempe, AZ (US)

(72) Inventor: Mohammad Nasser, Tempe, AZ (US)

(*) Notice: Subject to any disclaimer, the term of this patent is extended or adjusted under 35 U.S.C. 154(b) by 384 days.

(21) Appl. No.: 16/392,710

(22) Filed: Apr. 24, 2019

(65) Prior Publication Data

US 2020/0337586 A1   Oct. 29, 2020

(51) Int. Cl.
| | |
|---|---|
| *A61B 5/00* | (2006.01) |
| *A61B 5/055* | (2006.01) |
| *A61B 5/02* | (2006.01) |
| *G01R 33/28* | (2006.01) |
| *A61B 90/00* | (2016.01) |

(52) U.S. Cl.
CPC .......... *A61B 5/055* (2013.01); *A61B 5/02007* (2013.01); *G01R 33/285* (2013.01); *A61B 5/004* (2013.01); *A61B 5/6876* (2013.01); *A61B 2090/374* (2016.02)

(58) Field of Classification Search
CPC combination set(s) only.
See application file for complete search history.

(56) References Cited

U.S. PATENT DOCUMENTS

| | | | |
|---|---|---|---|
| 5,390,673 A | 2/1995 | Kikinis | |
| 7,588,535 B2 | 9/2009 | Adler | |
| 8,128,323 B2 | 3/2012 | Conroy | |
| 8,163,003 B2 | 4/2012 | Boyden | |
| D770,617 S | 11/2016 | Huang | |
| 2003/0199753 A1 | 10/2003 | Hibner | |
| 2016/0262638 A1 | 9/2016 | Kamada | |
| 2016/0320210 A1* | 11/2016 | Nelson | A61B 5/25 |

\* cited by examiner

*Primary Examiner* — Joel F Brutus

(57) ABSTRACT

An intravascular MRI probe assembly for producing real time, three dimension imagery of an interior of a blood vessel includes a probe has diameter is sufficiently small to fit inside of a blood vessel of a human being. An x coil, a y coil and a pair of z coils is each positioned within the probe for producing a magnetic field to facilitate magnetic resonance imaging of an interior of the blood vessel. A first gradient echo coil, a second gradient coil, a shim coil and a magnet is each positioned within the probe. A conductor is coupled to the probe and the conductor extends away from the second end of the probe. Additionally, the conductor is electrically coupled to a magnetic resonance imaging processor to produce a three dimensional image of the interior of the blood vessel.

9 Claims, 2 Drawing Sheets

INTRAVASCULAR MRI PROBE ASSEMBLY

CROSS-REFERENCE TO RELATED APPLICATIONS

Statement Regarding Federally Sponsored Research or Development

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to probe assemblies and more particularly pertains to a new probe assembly for producing real time, three dimensional imagery of an interior of a blood vessel.

BRIEF SUMMARY OF THE INVENTION

An embodiment of the disclosure meets the needs presented above by generally comprising a probe has diameter is sufficiently small to fit inside of a blood vessel of a human being. An x coil, a y coil and a pair of z coils is each positioned within the probe for producing a magnetic field to facilitate magnetic resonance imaging of an interior of the blood vessel. A first gradient echo coil, a second gradient coil, a shim coil and a magnet is each positioned within the probe. A conductor is coupled to the probe and the conductor extends away from the second end of the probe. Additionally, the conductor is electrically coupled to a magnetic resonance imaging processor to produce a three dimensional image of the interior of the blood vessel.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
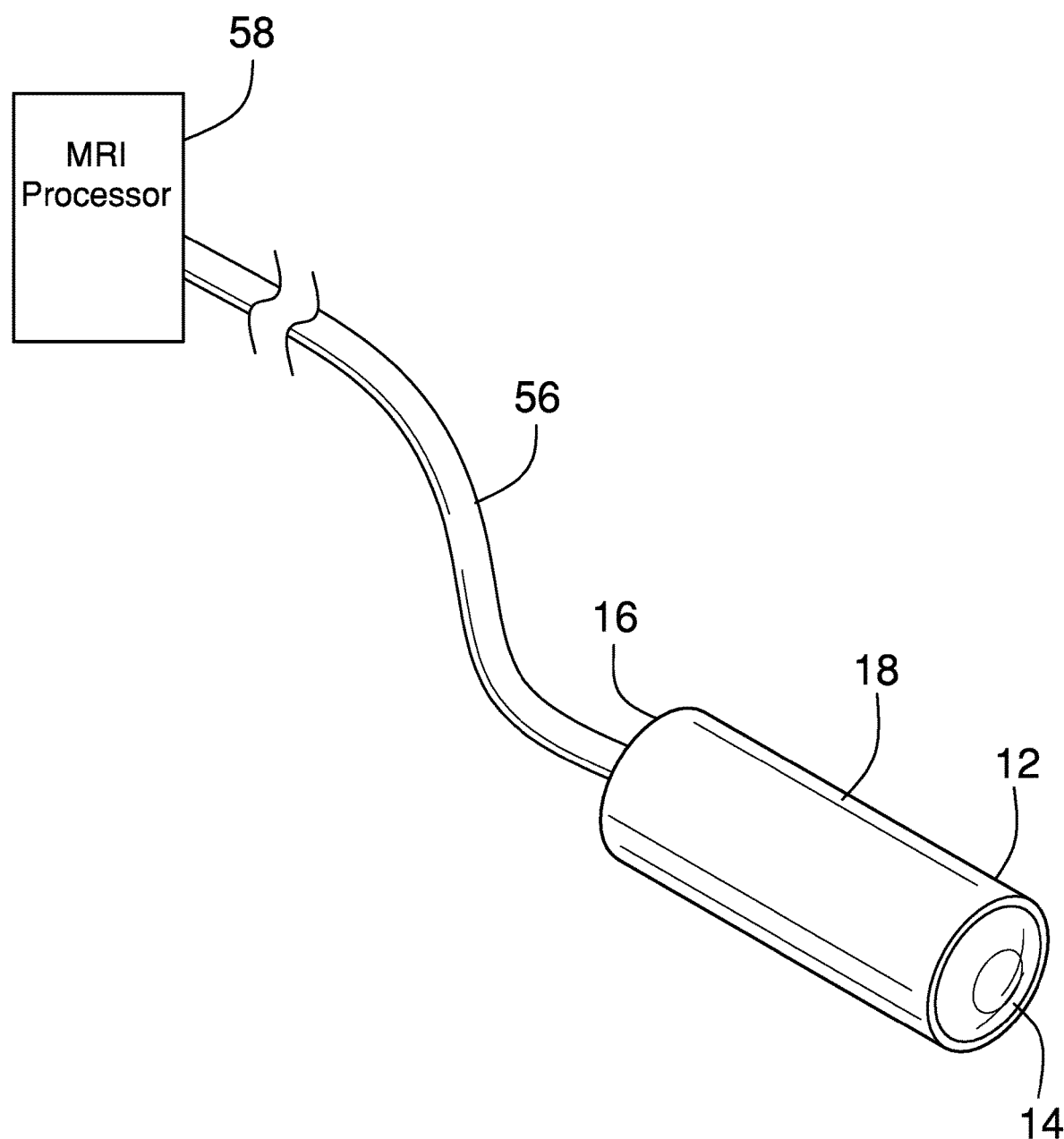
FIG. 1 is a perspective view of an intravascular MRI probe assembly according to an embodiment of the disclosure.
Figure 2:
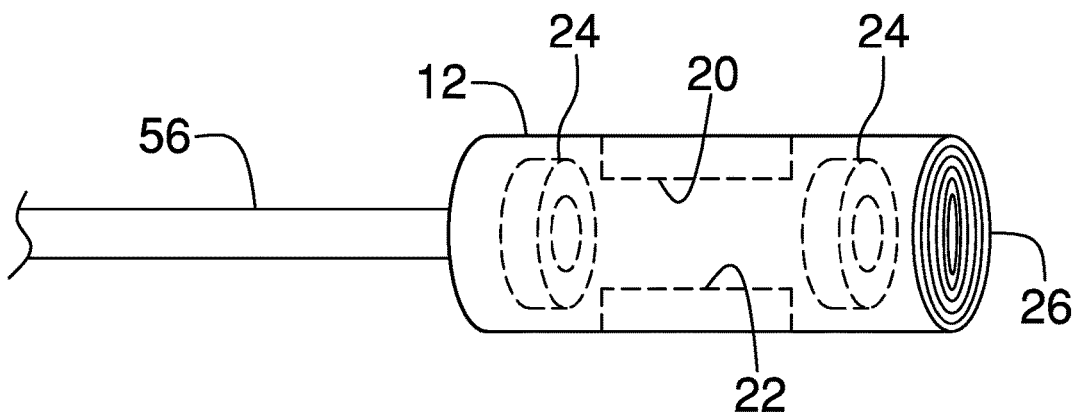
FIG. 2 is a right side phantom view of an embodiment of the disclosure.
Figure 3:
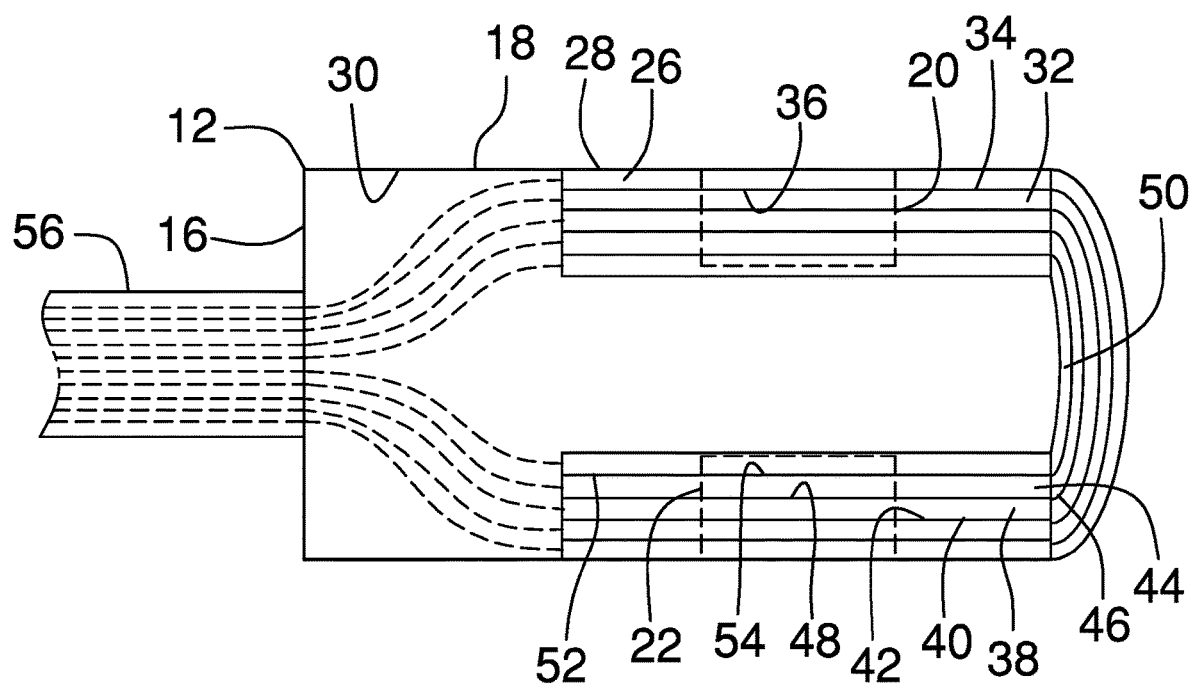
FIG. 3 is a right side cut-away view of an embodiment of the disclosure.

With reference now to the drawings, and in particular to FIGS. 1 through 3 thereof, a new probe assembly embodying the principles and concepts of an embodiment of the disclosure and generally designated by the reference numeral 10 will be described.

As best illustrated in FIGS. 1 through 3, the intravascular MRI probe assembly 10 generally comprises a probe 12 that has diameter being sufficiently small to fit inside of a blood vessel of a human being. Thus, the probe 12 can be catheterized into a blood vessel when a surgical procedure, such as inserting a stent or removing plaque from the blood vessel, is being performed. The probe 12 has a first end 14, a second end 16 and an outer wall 18 extending therebetween, and the outer wall 18 is continuously arcuate about an axis extending through the first 14 and second 16 ends such that the probe 12 has a cylindrical shape. Additionally, the probe 12 may be comprised of a hypo allergenic, surgical grade material that can be safely introduced into the blood vessel.

An x coil 20 is positioned within the probe 12 and the x coil 20 produces a magnetic field when the x coil 20 is turned on to facilitate magnetic resonance imaging of an interior of the blood vessel. The x coil 20 is centrally positioned between the first 14 and second 16 ends of the probe 12 and the x coil 20 may be a miniaturized version of a conventional x coil employed in existing, full sized MRI machines. A y coil 22 is positioned within the probe 12 and the y coil 22 produces a magnetic field when the y coil 22 is turned on to facilitate magnetic resonance imaging of an interior of the blood vessel. The y coil 22 is centrally positioned between the first 14 and second 16 ends of the probe 12 and the y coil 22 may be a miniaturized version of a conventional y coil employed in existing, full sized MRI machines.

A pair of z coils 24 is each of the z coils 24 is positioned within the probe 12. Each of the z coils 24 produces a magnetic field when the z coils 24 are turned on to facilitate magnetic resonance imaging of the interior of the blood vessel. Each of the z coils 24 is positioned adjacent to a respective one of first 14 and second 16 ends of the probe 12. Additionally, each of the z coils 24 may be a miniaturized version of conventional z coils 24 employed in existing, full sized MRI machines. Additionally, each of the x 20, y 22 and z 24 coils are oriented with respect to each other in the conventional orientation of x, y and z coils in existing, full sized MRI machines.

A first gradient echo coil 26 is positioned within the probe 12 to facilitate magnetic resonance imaging of the interior of the blood vessel. The first gradient echo coil 26 extends from the first end 14 of the probe 12 toward the second end 16 of the probe 12. The first gradient echo coil 26 has an outer surface 28 and the outer surface of the first gradient echo coil 26 is coextensive with an inside surface 30 of the outer wall 18 of the probe 12 such that the first gradient echo coil 26 defines a tube. The first gradient echo coil 26 may be a miniaturized version of an ultra high speed gradient echo coil employed in existing, full sized MRI machines.

A radio frequency coil 32 is positioned within the probe 12 to facilitate magnetic resonance imaging of the interior of the blood vessel. The radio frequency coil 32 extends from the first end 14 of the probe 12 toward the second end 16 of the probe 12. The radio frequency coil 32 has an outer surface 34 and the outer surface 34 of the radio frequency coil 32 is coextensive with an interior surface 36 of the first gradient echo coil 26 such that the radio frequency coil 32 defines a tube. Additionally, the radio frequency coil 32 may be a miniaturized version of a radio frequency coil employed in existing, full sized MRI machines.

A second gradient coil 38 is positioned within the probe 12 to facilitate magnetic resonance imaging of the interior of the blood vessel. The second gradient coil 38 extends from the first end 14 of the probe 12 toward the second end 16 of the probe 12. The second gradient coil 38 has an outer surface 40 and the outer surface 40 of the second gradient coil 38 is coextensive with an interior surface 42 of the radio frequency coil 32 such that the second gradient coil 38 defines a tube. The second gradient coil 38 may be a miniaturized version of a gradient coil employed in conventional, full sized MRI machines.

A shim coil 44 is positioned within the probe 12 and the shim coil 44 extends from the first end 14 of the probe 12 toward the second end 16 of the probe 12. The shim coil 44 has an outer surface 46 and the outer surface 46 of the shim coil 44 is coextensive with an interior surface 48 of the second gradient coil 38 such the shim coil 44 defines a tube. The shim coil 44 may be a miniaturized version of an active shim coil 44 employed in conventional, full sized MRI machines.

A magnet 50 is positioned within the probe 12 and the magnet 50 extends from the first end 14 of the probe 12 toward the second end 16 of the probe 12. The magnet 50 has an outer surface 52 and the outer surface 52 of the magnet 50 is coextensive with an interior surface 54 of the shim coil 44 such that the magnet 50 defines a tube. The magnet 50 may be an electromagnet that produces a magnetic field which is similar both in strength and orientation with respect to that which is commonly employed in conventional, full sized MRI machines.

A conductor 56 is coupled to the probe 12 and the conductor 56 is in electrical communication with each of the first gradient echo coil 26, the radio frequency coil 32, the second gradient coil 38, the shim coil 44 and the magnet 50. The conductor 56 extends away from the second end 16 of the probe 12 and the conductor 56 may be shielded with a hypo allergenic, surgical grade material that can be safely introduced into the blood vessel. The conductor 56 is electrically coupled to a magnetic resonance imaging processor 58 to produce a three dimensional image of the interior of the blood vessel.

In use, the probe 12 is inserted into the blood vessel through conventional catheterization techniques with respect to blood vessels. Moreover, the probe 12 is inserted into the blood vessel when imaging of the interior of the blood vessel is required for guiding a surgical procedure within the blood vessel. In this way an MRI image can be produced, in real time, of the interior of the blood vessel. Thus, a surgeon can have access to comprehensive imagery of the interior of the blood vessel for guidance during surgical procedures that are performed within blood vessels. In this way the surgeon can perform the surgical procedure with more information and guidance than could otherwise be achieved with the introduction of dye into the blood vessel and subsequent exposure of the blood vessel to X-ray radiation. Thus, imaging of the interior of the blood vessel can be achieved without posing a cancer risk to the surgeon or the patient resulting from exposure to X-ray radiation.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An intravascular MRI probe assembly being configured to be inserted into a blood vessel for imaging an interior of the blood vessel, said intravascular MRI assembly comprising:

a probe having a first end and a second end, said probe having a diameter being sufficiently small such that said probe is configured to fit inside of a blood vessel of a human being;

an x coil being positioned within said probe, said x coil being configured to produce a magnetic field when said x coil is turned on wherein said x coil is configured to facilitate magnetic resonance imaging of an interior of the blood vessel;

a y coil being positioned within said probe, said y coil producing a magnetic field when said y coil is turned on wherein said y coil is configured to facilitate magnetic resonance imaging of an interior of the blood vessel;

a pair of z coils, each of said z coils being positioned within said probe, each of said z coils producing a magnetic field when said z coils are turned on wherein said z coils are configured to facilitate magnetic resonance imaging of the interior of the blood vessel;

a first gradient echo coil being positioned within said probe wherein said first gradient echo coil is configured to facilitate magnetic resonance imaging;

a radio frequency coil being positioned within said probe wherein said radio frequency coil is configured to facilitate magnetic resonance imaging;

a second gradient coil being positioned within said probe wherein said second gradient coil is configured to facilitate magnetic resonance imaging;
a shim coil being positioned within said probe;
a magnet being positioned within said probe; and
a conductor being coupled to said probe, said conductor being in electrical communication with each of said first gradient echo coil, said radio frequency coil, said second gradient coil, said shim coil and said magnet, said conductor being configured to extend away from said second end of said probe, said conductor being electrically coupled to a magnetic resonance imaging processor wherein said magnetic imaging processor is configured to produce a three dimensional image of the interior of the blood vessel.

2. The intravascular MRI probe assembly according to claim 1, wherein said probe has an outer wall configured to extend between said first end of said probe and said second end of said probe, said outer wall being continuously arcuate about an axis configured to extend through said first end and said second end such that said probe has a cylindrical shape.

3. The intravascular MRI probe assembly according to claim 2, wherein:
said x coil is centrally positioned between said first end and said second end of said probe;
said y coil is centrally positioned between said first end and said second end of said probe; and
each of said z coils is positioned adjacent to a respective one of first end and said second end of said probe.

4. The intravascular MRI probe assembly according to claim 2, wherein said first gradient echo coil extends from said first end of said probe toward said second end of said probe, said first gradient coil having an outer surface, said outer surface of said first gradient echo coil being coextensive with an inside surface of said outer wall of said probe such that said first gradient echo coil defines a tube.

5. The intravascular MRI probe assembly according to claim 4, further wherein said radio frequency coil extends from said first end of said probe toward said second end of said probe, said radio frequency coil having an outer surface, said outer surface of said radio frequency coil being coextensive with an interior surface of said first gradient echo coil such that said radio frequency coil defines a tube.

6. The intravascular MRI probe assembly according to claim 5, wherein said second gradient coil extends from said first end of said probe toward said second end of said probe, said second gradient coil having an outer surface, said outer surface of said second gradient coil being coextensive with an interior surface of said radio frequency coil such that said second gradient coil defines a tube.

7. The intravascular MRI probe assembly according to claim 6, wherein said shim coil extends from said first end of said probe toward said second end of said probe, said shim coil having an outer surface, said outer surface of said shim coil being coextensive with an interior surface of said second gradient coil such said shim coil defines a tube.

8. The intravascular MRI probe assembly according to claim 7, wherein said magnet extends from said first end of said probe toward said second end of said probe, said magnet having an outer surface, said outer surface of said magnet being coextensive with an interior surface of said shim coil such that said magnet defines a tube.

9. An intravascular MRI probe assembly being configured to be inserted into a blood vessel for imaging an interior of the blood vessel, said intravascular MRI probe assembly comprising:

a probe having a diameter being sufficiently small such that said probe is configured to fit inside of a blood vessel of a human being, said probe having a first end, a second end and an outer wall configured to extend therebetween, said outer wall being continuously arcuate about an axis configured to extend through said first end and said second end such that said probe has a cylindrical shape;
an x coil being positioned within said probe, said x coil configured to produce a magnetic field when said x coil is turned on wherein said x coil is configured to facilitate magnetic resonance imaging of an interior of the blood vessel, said x coil being centrally positioned between said first end and said second end of said probe;
a y coil being positioned within said probe, said y coil configured to produce a magnetic field when said y coil is turned on wherein said y coil is configured to facilitate magnetic resonance imaging of an interior of the blood vessel, said y coil being centrally positioned between said first end and said second end of said probe;
a pair of z coils, each of said z coils being positioned within said probe, each of said z coils configured to produce a magnetic field when said z coils are turned on wherein said z coils are configured to facilitate magnetic resonance imaging of the interior of the blood vessel, each of said z coils being positioned adjacent to a respective one of first end and said second end of said probe;
a first gradient echo coil being positioned within said probe wherein said first gradient echo coil is configured to facilitate magnetic resonance imaging, said first gradient echo coil being configured to extend from said first end of said probe toward said second end of said probe, said first gradient coil having an outer surface, said outer surface of said first gradient echo coil being coextensive with an inside surface of said outer wall of said probe such that said first gradient echo coil defines a tube;
a radio frequency coil being positioned within said probe wherein said radio frequency coil is configured to facilitate magnetic resonance imaging, said radio frequency coil configured to extend from said first end of said probe toward said second end of said probe, said radio frequency coil having an outer surface, said outer surface of said radio frequency coil being coextensive with an interior surface of said first gradient echo coil such that said radio frequency coil defines a tube;
a second gradient coil being positioned within said probe wherein said second gradient coil is configured to facilitate magnetic resonance imaging, said second gradient coil configured to extend from said first end of said probe toward said second end of said probe, said second gradient coil having an outer surface, said outer surface of said second gradient coil being coextensive with an interior surface of said radio frequency coil such that said second gradient coil defines a tube;
a shim coil being positioned within said probe, said shim coil configured to extend from said first end of said probe toward said second end of said probe, said shim coil having an outer surface, said outer surface of said shim coil being coextensive with an interior surface of said second gradient coil such said shim coil defines a tube;
a magnet being positioned within said probe, said magnet configured to extend from said first end of said probe toward said second end of said probe, said magnet having an outer surface, said outer surface of said magnet being coextensive with an interior surface of said shim coil such that said magnet defines a tube; and a conductor being coupled to said probe, said conductor being in electrical communication with each of said first gradient echo coil, said radio frequency coil, said second gradient coil, said shim coil and said magnet, said conductor configured to extend away from said second end of said probe, said conductor being electrically coupled to a magnetic resonance imaging processor wherein said magnetic imaging processor is configured to produce a three dimensional image of the interior of the blood vessel.

* * * * *